United States Patent [19]
Podesva et al.

[11] 3,957,776

[45] May 18, 1976

[54] NOVEL PHTHALAZINONE COMPOUNDS

[75] Inventors: Ctirad Podesva, Montreal; Lise A. Hughes, Ville de Lery, both of Canada

[73] Assignee: Delmar Chemicals Limited, Ville LaSalle, Canada

[22] Filed: Feb. 28, 1973

[21] Appl. No.: 336,740

[52] U.S. Cl. .................. 260/247.2 A; 260/243 B; 260/250 P; 260/268 BC; 424/246
[51] Int. Cl.² .................................. C07D 295/00
[58] Field of Search .............. 260/247.2 A, 250 A, 260/250 P

[56] References Cited
OTHER PUBLICATIONS

Rylski, L. et al., Acta Poloniae Pharmaceutica XXII No. 2 pp. 119–124 1965.

*Primary Examiner*—Paul J. Killos
*Attorney, Agent, or Firm*—Christen & Sabol

[57] ABSTRACT

Certain 2-substituted-4-substituted-1(2H)-phthalazinone compounds have hypotensive activity. Such compounds are used in pharmaceutical compositions. Processes of preparing them and the intermediate compounds are disclosed.

25 Claims, No Drawings

NOVEL PHTHALAZINONE COMPOUNDS

The present invention relates to certain organic compounds broadly classified as phthalazine derivatives. More particularly, this invention is concerned with 2-substituted-4-substituted-1(2H)-phthalazinone compounds, with processes for preparing them, and pharmaceutical compositions containing them, and intermediate compounds useful in the preparation thereof.

It has been found that certain new phthalazine derivatives as hereinafter defined possess hypotensive activity, as evidenced, by standard pharmacological evaluation.

According to this invention, therefore, in one of its aspects, there are provided phthalazine derivatives of the following general formula:

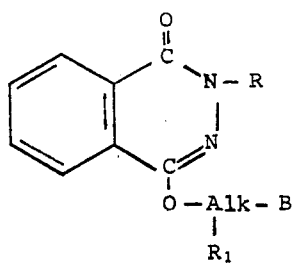

(I)

and acid addition and quaternary ammonium salts thereof; wherein R represents a lower alkyl, an aryl or a lower aralkyl group; Alk represents a lower alkylene group; $R_1$ represents a free or substituted hydroxyl group and B represents an amino group.

The term "lower" as used herein in the context of alkyl, aralkyl and alkylene groups connotes such groups as contain no more than 6 carbon atoms.

In the above compounds wherein R is a lower alkyl group, this may for example, be a methyl, an ethyl, a propyl, an isopropyl, a butyl, an isobutyl, a secondary butyl or a tertiary butyl group. In those instances, wherein R is an aryl group, this may, for example, be a phenyl or a substituted phenyl group. In those instances wherein R is a lower aralkyl group, this may, for example, be a benzyl, a 1-phenylethyl, a 2-phenylethyl or a 1-phenylpropyl group.

The divalent lower alkylene group represented by the symbol Alk in the compounds of Formula I, is a divalent saturated aliphatic hydrocarbon radical derived from a straight or branched-chain hydrocarbon residue such as, for example, ethylene, propylene, butylene, trimethylene, tetramethylene, 1-methylethylene. Such alkylene radicals may include substituents in addition to the hydroxyl groups.

Among suitable amino groups included within the symbol B are primary, secondary and tertiary amino groups, such as unsubstituted amino (-NH₂), (lower alkyl)-amino; di-(lower alkyl)-amino; (lower alkenyl)-amino; di-(lower alkenyl)-amino; (amino-lower alkyl)-amino; di-(amino-lower alkyl)-amino phenylamino; (hydroxy-lower alkyl)-amino; di-(hydroxy-lower alkyl)-amino; basic heterocyclic radicals of less than 12 carbon atoms as exemplified by piperidino; (lower alkyl)-piperidino, e.g. 2-,3-, or 4-(lower alkyl)-piperidino; di-(lower alkyl)-piperidino, e.g. 2,4-,2,6-, or 3,5-di-(lower alkyl)-piperidino; (lower alkoxy)-piperidino; pyrrolidino; (lower alkyl)-pyrrolidino; di-(lower alkyl)-pyrrolidino; (lower alkoxy)-pyrrolidino; morpholino; (lower alkyl)-morpholino; di-(lower alkyl)-morpholino; (lower alkoxy)-morpholino; thiomorpholino; (lower alkyl)-thiomorpholino; di-(lower alkyl)-thiomorpholino; (lower alkoxy)-thiomorpholino; piperazino; (lower alkyl)-piperazino, (e.g. C or N4 methyl piperazino); di-C-(lower alkyl)-piperazino; N-(hydroxy-lower alkyl)-piperazino; (lower alkoxy)-piperazino and (lower carbalkoxy)-piperazino.

It has been found that the compounds defined by Formula I, in standard pharmacological evaluation, demonstrate hypotensive activity indicative of potential utility as antihypertensive agents to relieve conditions such as, for example, neurogenic or renal hypertension.

A pharmaceutically preferred group of compounds within the broad class defined by Formula I are compounds having the following formula:

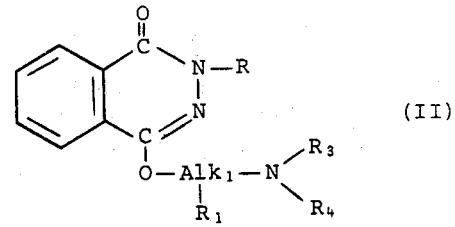

(II)

and acid addition and quaternary ammonium salts thereof; wherein R and $R_1$ have the same significance as hereinbefore, $Alk_1$ represents a straight or branched-chain lower alkylene group interposing at least 3 carbon atoms in a direct or straight line between the oxygen and nitrogen atoms, $R_3$ and $R_4$, when taken separately, are the same, or different, and each represents a hydrogen atom, a lower alkyl, aryl or lower aralkyl group or, when taken together with the nitrogen atom to which they are attached, represent a 5- or 6-membered heterocyclic ring. Within this preferred class, compounds which appear particularly interesting are those wherein: R is a lower alkyl group, especially methyl; $Alk_1$ is a 2-hydroxy-propylene group, i.e.

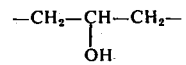

$R_3$ is a hydrogen atom when $R_4$ is a lower alkyl or a phenyl-lower alkyl group, e.g. benzyl; or
$R_3$ and $R_4$ are both lower alkyl groups or taken together with the nitrogen atom to which they are attached, are a pyrrolidino, a piperidino, a morpholino, a piperazino or a 4-(lower alkyl)-piperazino group.

Specifically preferred compounds of the Formula II in view of their favorable activity are:
2-methyl-4-(2'-hydroxy-3'-isopropylamino)-propoxy-1(2H)-phthalazinone;
2-methyl-4-[2'-hydroxy-3'-(tert.-butylamino)]-propoxy-1(2H)-phthalazinone;
2-methyl-4-[2'-hydroxy-3'-(3-phenyl-1-propylamino)]-propoxy-1(2H)-phthalazinone;
2-methyl-4-[2'-hydroxy-3'-(sec.-butylamino)]-propoxy-1(2H)-phthalazinone;
2-methyl-4-[2'-hydroxy-3'-dimethylamino)-propoxy-1(2H)-phthalazinone;

2-methyl-4-(2'-hydroxy-3'-piperidino)-propoxy-1-(2H)-phthalazinone; and 2-methyl-4-[2'-hydroxy-3'-(N-methyl piperazino)]-propoxy-1(2H)-phthalazinone.

Another pharmaceutically preferred group of compounds within the broad class defined by Formula 1, are compounds having the following formula:

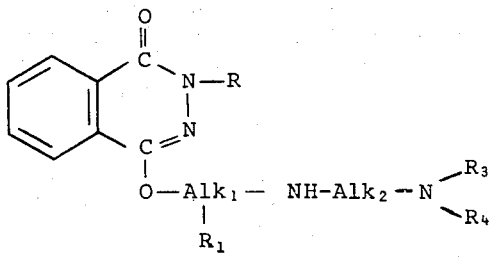

and acid addition salts thereof; wherein R, Alk$_1$, R$_1$, R$_3$ and R$_4$ have the same significance as hereinbefore and Alk$_2$ represents a divalent lower alkylene group. Within this preferred class, compounds which appear particularly interesting are those wherein: R is a lower alkyl group, especially methyl; Alk$_1$ is a 2-hydroxy propylene group, i.e.

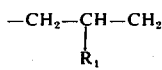

Alk$_2$ is methylene, ethylene or propylene; and R$_3$ and R$_4$ are both lower alkyl groups, or taken together with the nitrogen atom to which they are attached are a pyrrolidino, a piperidino, a morpholino, a piperazino, or a 4-(lower alkyl)-piperazino group.

Specifically preferred compounds of the Formula III in view of their favorable activity are:

2-methyl-4-[2'-hydroxy-3'-(3-dimethylamino-propylamino)]-propoxy-1(2H)-phthalazinone;

2-methyl-4-[2'-hydroxy-3'-(3-diethylamino-propylamino)]-propoxy-1(2H)-phthalazinone;

2-methyl-4-[2'-hydroxy-3'-(unsym.-dimethylethylenediamine)]-propoxy-1(2H)-phthalazinone;

2-methyl-4-[2'hydroxy-3'-(N,N-diethylethylenediamine)]-propoxy-1(2H)-phthalazinone;

2-methyl-4-[2'-hydroxy-3'-(N-2-aminoethyl)-morpholino]-propoxy-1(2H)-phthalazinone, and 2-methyl-4-[2'-hydroxy-3'-(N-3-amino-propyl)-morpholine]-propoxy-1 (2H)-phthalazinone.

As is evident from the Formulae I to III, the novel compounds contain one or more basic nitrogen atoms which can react with acids to form acid addition and quaternary ammonium salts. The acid addition salts are readily prepared by reacting together stoichiometrically equivalent amounts of the desired base and a selected acid in a mutual solvent.

When the compounds are to be used as pharmaceuticals, they are most conveniently used in the form of water-soluble, non-toxic, acid addition salts.

When compounds are to be used as intermediates for preparing other compounds or for any other non-pharmaceutical use, the toxicity or non-toxicity of the salt is usually immaterial. Both toxic and non-toxic salts are, therefore, within the purview of this invention. The acids which can be used to prepare the preferred non-toxic, acid addition salts are those which produce, when combined with the free bases, salts whose anions are relatively innocuous to the animal organism in therapeutic doses of the salts so that the beneficial physiological properties inherent in the free bases are not vitiated by side-effects ascribable to the anions. Appropriate acid addition salts are those derived from mineral acids such as, for example, hydrochloric acid, hydrobromic acid, hydriodic acid, nitric acid, boric acid and phosphoric acid; and organic acids such as, for example, acetic acid, tartaric acid, citric acid, succinic acid, lactic acid and maleic acid.

The new compounds according to this invention may be prepared by any desired method.

Conveniently, the starting compounds used in the preparation of the desired compounds is an appropriate 2R- 2,3-dihydro-1,4-phthalazinedione which are either known compounds or can be readily obtained following standard chemical procedures [cf. Elderfield: Heterocyclic Compounds, Volume 6, p 223; Blanksma et al.: Rec. trav. chim 58, 497 (1939); Rowe et al.: J.C.S. 1331, (1933).] For instance, they may be prepared by reacting, for example, by heating in the presence of a solvent phthalic anhydride or other suitable dicarbonyl compound, such as a diester, with a substituted hydrazine of the formula:

in which R has the same significance as hereinbefore.

Alternatively, 2-(lower alkyl)-2,3-dihydro-1,4-phthalazinedione compounds may be prepared by alkylation of phthalyl hydrazide, say, with a dialkyl sulfate, followed by selective desalkylation, if necessary.

Subsequently, the 2R-2,3-dihydro-1,4-phthalazinedione must be treated in such a way as to introduce the alkylene-amino moiety

at the 4-position. In one approach, this is accomplished in two stages with the initial introduction of the alkylene group followed by introduction of the amino group. Suitable procedures for introducing the alkylene group include, for instance, reaction of phthalazinedione with sodium metal and an appropriate alkylene halide or reaction of the phthalazinedione with an alkylene-containing reactant bearing a labile leaving group, such as, for example, a tosyl group, in the presence of a strong base such as sodium or potassium hydroxide or alkoxide. The alkylene reactant should contain a further reactive group, such as, for example, an epoxide radical, replaceable by the amino group B in a subsequent reaction step. Suitable procedures for introducing the amino group (B) include, for example, reaction of the 2-R-4-alkylene-2,3-dihydro-1,4-phthalazinedione with the appropriate amine.

In an alternative approach to the preparation of the desired compounds of Formula I, the alkylene-amino moiety may be introduced in a single reaction step by reacting an alkylene-amino-halide of the formula:

wherein Alk, B and R have the same significance as hereinbefore and X is a halogen atom, with the 2R-2,3-dihydro-1,4-phthalazinedione. If desired, the alkylene halide may have as a part of its structure, a suitable protected amino function, i.e. phthaloylated and, after the condensation reaction with the phthalazinedione compound has been effected, the protected amine can be conveniently transformed into the free amine or any desired monoalkyl or dialkyl amines by suitable procedures for removing the protective group and, if necessary, alkylation of the resultant free amine.

alkoxy-1(2H)-phthalazinone compounds are themselves novel, and constitute a further feature of this invention. The epoxy compound is then treated with an appropriate amine whereupon the amine adds to the epoxide group with ring cleavage and generation of the free hydroxyl group to form the desired compounds of Formula I. This process as applied to the preparation of representative compounds of Formula I, namely, 2-alkyl-4-(2'-hydroxy-3'-alkylamino)-propoxy-1(2H)-phthalazinones is illustrated in the following flow sheet:

FLOW SHEET

STEP 1

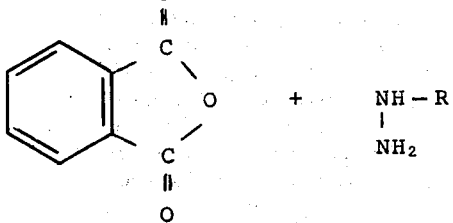

STEP 2

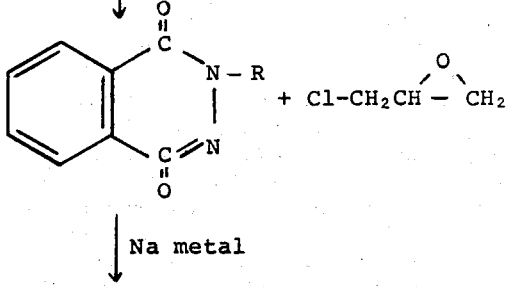

STEP 3

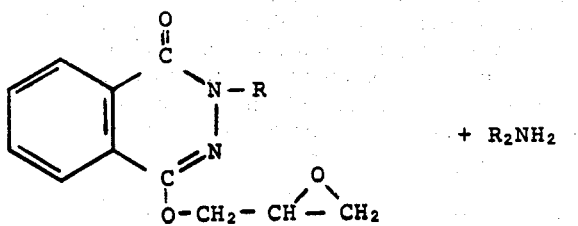

(Novel Compounds)

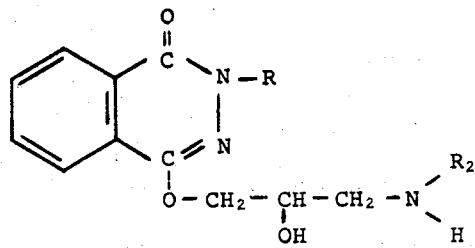

In a preferred process for making the compounds of Formula I, a 2-R-2,3-dihydro-1,4-phthalazinedione is reacted, for example, by heating in a solvent and in the presence of sodium metal with an appropriate epoxy substituted alkylene halide such as, for example, epichlorohydrin (1-chloro-2,3-epoxypropane) to give the corresponding 2-R-4-(2',3'-epoxy)-alkoxy-1(2H)-phthalazinone compound. These 2-R-4-(2',3'-epoxy)-

The invention will appear more fully from a consideration of the following examples. However, it should be understood that these examples are given by way of illustration only and that the invention is not to be construed as limited in spirit or scope by the details set forth herein. In these examples, temperatures are given uncorrected in degrees centigrade (°C.), and melting points were determined by the capillary tube method.

Example 1

2-Methyl-4-(2'-hydroxy-3'-isopropylamino)-propoxy-1-(2H)-phthalazinone

2-Methyl-4-(2',3'-epoxy)-propoxy-1(2H)-phthalazinone.

12 G. (0.068 mole) of 2-methyl-2,3-dihydro-1,4-phthalazinedione (Elderfield, Heterocyclic Compounds, Vol.6, p. 223) were added to a solution of 1.56 g. (0.068 mole) of sodium in 120 ml. of absolute methanol. The solution was refluxed 15 minutes and, thereafter, 240 ml. of epichlorohydrin added. The resultant mixture was refluxed for 5 hours and then allowed to stand at room temperature 18 hours, whereupon the suspension was filtered to remove sodium chloride and the filtrate evaporated in vacuo. The pale yellow oil which resulted was subsequently dissolved in 250 ml. of chloroform, washed (twice) with 100 ml. of water, dried over sodium sulfate, filtered, and the chloroform evaporated in vacuo. The pale yellow oil was dissolved in 75 ml. ethylacetate and set aside to crystallize at 5°. Melting Point: 135° to 136°.

Part B 2-Methyl-4-(2'-hydroxy-3'-isopropylamino)-propoxy-1(2H)-phthalazinone.

2.32 G. (0.01 mole) of 2-methyl-4-(2',3'-epoxy)-propoxy-1(2H)-phthalazinone obtained by the procedure as set forth in Part A were dissolved in 7 ml. of absolute methanol and 1.8 g. (0.03 mole) of isopropylamine were added. The solution was gently refluxed for 18 hours, cooled to room temperature, diluted with 7 ml. of water and enough glacial acetic acid to give a pH of 5. The solution was washed with 25 ml. of chloroform and the aqueous extract basified with 30% sodium hydroxide to pH 14 while cooling so as to maintain the temperature at less than 20°. The suspension was extracted (twice) with 50 ml. of chloroform, dried over sodium sulfate, filtered and the chloroform evaporated in vacuo. The pale yellow resin was treated with 25 ml. of dry ether and set aside to crystallize at 5°C. An analysis sample was recrystallized from ethyl acetate. Melting point: 115° to 116°.

Elementary analysis:

|  | C(%) | H(%) | N(%) |
|---|---|---|---|
| Calculated $C_{15}H_{21}N_3O_3$ | 61.83 | 7.27 | 14.42 |
| Found | 62.07 | 7.27 | 14.24 |

Example 2

2-Methyl-4-[2'-hydroxy-3'-(tert-butylamino)-propoxy-1(2H) phthalazinone

This compound was prepared following essentially the same procedure as set forth in Part B of Example 1 using 2.32 g. (0.01 mole) of 2-methyl-4-(2',3'-epoxy)-propoxy-1(2H)-phthalazinone and 2.2 g. (0.03 mole) of tert-butylamine. An analysis sample was recrystallized from ether. Melting point: 112° to 113°.

Elementary analysis:

|  | C(%) | H(%) | N(%) |
|---|---|---|---|
| Calculated $C_{16}H_{23}N_3O_3$ | 62.93 | 7.59 | 13.76 |
| Found | 62.82 | 7.47 | 13.50 |

Example 3

2-Methyl-4-[2'-hydroxy-3'-(3-phenyl-1-propylamino)] propoxy-1(2H)-phthalazinone

This compound was prepared following essentially the same procedure as set forth in Part B of Example 1 using 2.32 g. (0.01 mole) of 2-methyl-4-(2',3'-epoxy)-propoxy-1-(2H)-phthalazinone and 4 g. (0.03 mole) of 3-phenyl-1-propylamine. An analysis sample was recrystallized from ethyl acetate. Melting point: 112° to 114°.

Elementary analysis:

|  | C(%) | H(%) | N(%) |
|---|---|---|---|
| Calculated $C_{21}H_{25}N_3O_3$ | 68.64 | 6.86 | 11.44 |
| Found | 68.49 | 6.94 | 11.75 |

Example 4

2-Methyl-4-[2'-hydroxy-3'-(sec-butylamino)]-propoxy-1(2H)-phthalazinone

This compound was prepared following essentially the same procedure as set forth in Part B of Example 1 using 2.32 g. (0.01 mole) of 2-methyl-4-(2',3'-epoxy)-propoxy-1(2H)-phthalazinone and 2.2g. (0.03 mole) of sec-butylamine. An analysis sample was recrystallized from ether. Melting point: 77° to 78°.

elementary analysis:

|  | C(%) | H(%) | N(%) |
|---|---|---|---|
| Calculated $C_{16}H_{23}N_3O_3$ | 62.93 | 7.59 | 13.76 |
| Found | 62.65 | 7.20 | 13.86 |

Example 5

2-Methyl-4-[2'-hydroxy-3'-(3-dimethylaminopropylamino)]-propoxy-1(2H) phthalazinone This compound was prepared following essentially the same procedure as set forth in Part B of Example 1 using 2.32 g. (0.01 mole) of 2-methyl-4-(2',3'-epoxy)-propoxy-1(2H)-phthalazinone and 3.0 g. (0.03 mole) of 3-dimethylaminopropylamine. An analysis simple was recrystallized from ethyl acetate. Melting point: 88° to 90°.

Elementary analysis:

|  | C(%) | H(%) | N(%) |
|---|---|---|---|
| Calculated $C_{17}H_{26}N_4O_3$ | 61.05 | 7.83 | 16.75 |
| Found | 61.36 | 7.70 | 17.00 |

Example 6

2-Methyl-4-[2'-hydroxy-3'-diethylaminopropylamino)]-propoxy-1(2H)-phthalazinone

This compound was prepared following essentially the same procedure as set forth in Part B of Example 1 using 2.32 g. (0.01 mole) of 2-methyl-4-(2',3'-epoxy)-propoxy-1(2H)-phthalazinone and 4 g. (0.003 mole) of 3-diethylaminopropylamine. An analysis sample was recrystallized from ether. Melting point: 79° to 80°.

Elementary analysis:

|  | C(%) | H(%) | N(%) |
|---|---|---|---|
| Calculated $C_{19}H_{30}N_4O_3$ | 62.95 | 8.34 | 15.46 |
| Found | 63.10 | 8.13 | 15.61 |

Example 7

2-Methyl-4-[2'hydroxy-3'-(unsym.-dimethylethylenediamine)]-propoxy-1(2H)-phthalazinone This compound was prepared following essentially the same procedure as set forth in Part B of Example 1 using 2.32 g. (0.01 mole) of 2-methyl-4-(2',3'-epoxy)-propoxy-1-(2H)-phthalazinone and 2.5 g. (0.003 mole) of unsym.-dimethylethylenediamine. An analysis sample was recrystallized from ethyl acetate. Melting point: 109° to 110°.

Elementary analysis:

|  | C(%) | H(%) | N(%) |
|---|---|---|---|
| Calculated $C_{16}H_{24}N_4O_3$ | 59.97 | 7.55 | 17.48 |
| Found | 59.66 | 7.32 | 17.29 |

Example 8

2-Methyl-4-[2'-hydroxy-3'-(N,N,diethylethylenediamine)]-propoxy-1(2H)-phthalazinone This compound was prepared following essentially the same procedure as set forth in Part B of Example 1 using 2.32 g. (0.01 mole) of 2-methyl-4-(2',3'-epoxy)-propoxy-1-(2H)-phthalazinone and 3.5 g. (0.03 mole) of N,N-diethylethylenediamine. An analysis sample was recrystallized from ethyl acetate. Melting point: 90° to 92°.

Elementary analysis:

|  | C(%) | H(%) | N(%) |
|---|---|---|---|
| Calculated $C_{18}H_{28}N_4O_3$ | 62.04 | 8.09 | 16.08 |
| Found | 61.76 | 8.27 | 15.81 |

Example 9

2-Methyl-4-[2'-hydroxy-3'-(N-2-aminoethyl)-morpholino]-propoxy-1(2H)-phthalazinone This compound was prepared following essentially the same procedure as set forth in Part B of Example 1 using 2.32 g. (0.01 mole) of 2-methyl-4-(2',3'-epoxy)-propoxy-1-(2H)-phthalazinone and 4.0 g. (0.03 mole) of N-(2-aminoethyl)-morpholine. An analysis sample was recrystallized from ethyl acetate. Melting point: 107° to 108°.

Elementary analysis:

|  | C(%) | H(%) | N(%) |
|---|---|---|---|
| Calculated $C_{18}H_{26}N_4O_4$ | 59.64 | 7.23 | 15.45 |
| Found | 59.35 | 7.23 | 15.22 |

Example 10

2-Methyl-4-[2'-hydroxy-3'-(N-3-aminopropyl)-morpholino]-propoxy-1 (2H)-phthalazinone This compound was prepared following essentially the same procedure as set forth in Part B of Example 1 using 2.32 g. (0.01 mole) of 2-methyl-4-(2',2'-epoxy)-propoxy-1-(2H)-phthalazinone and 4.0 g. (0.03 mole) of N-(3-aminopropyl)-morpholine. An analysis sample wss recrystallized from ethyl acetate. Melting point: 100° to 102°.

Elementary analysis:

|  | C(%) | H(%) | N(%) |
|---|---|---|---|
| Calculated $C_{19}H_{28}N_4O_4$ | 60.61 | 7.50 | 14.88 |
| Found | 60.41 | 7.60 | 14.67 |

Example 11

2-Methyl-4-(2'-hydroxy-3'-dimethylamino)-propoxy-1(2H)-phthalazinone 2.32 G. (0.01 mole) of 2-methyl-4-(2',3'-epoxy)-propoxy-1(2H)-phthalazinone were added to 7 ml. of absolute methanol which had previously been saturated with dimethylamine. The mixture was stirred at room temperature for 48 hours whereupon a clear solution was obtained. This solution was diluted with 7 ml. of water and enough acetic acid to give a pH of 5. The solution was washed with 25 ml. of chloroform and the aqueous phase basified with 30% sodium hydroxide to pH 14 while cooling so as to maintain the temperature of the solution no higher than 20°. The suspension was extracted (twice) with 50 ml. of chloroform, dried over sodium sulfate, filtered, and the chloroform evaporated in vacuo. The resultant pale yellow oil was treated with 25 ml. of ether to produce on cooling at 5° an off-white crystalline solid. An analysis sample was recrystallized from ethyl acetate. Melting point: 94° to 95°.

Elementary analysis:

|  | C(%) | H(%) | N(%) |
|---|---|---|---|
| Calculated $C_{14}H_{19}N_3O_3$ | 60.60 | 6.91 | 15.15 |
| Found | 60.29 | 6.81 | 15.39 |

Example 12

2-Methyl-4-(2'-hydroxy-3'-piperidino)-propoxy-1(2H)-phthalazinone 2.32 G. (0.01 mole) of 2-methyl-4-(2',3'-epoxy)-propoxy-1(2H)-phthalazinone were dissolved in 7 ml. of methanol and 0.9 g. (0.011 mole) of piperidine were added. The solution was refluxed for 18 hours, cooled to room temperature, diluted with 25 ml. of 10% hydrochloric acid and washed with 25 ml. of chloroform. The aqueous phase was basified with 30% sodium hydroxide to pH14 while cooling so as to maintain the temperature below 20°. The suspension was extracted (twice) with 50 ml. of chloroform, dried over sodium sulfate, filtered and the chloroform evaporated in vacuo. The resultant pale yellow resin was treated with 25 ml. of ether to yield an off-white crystalline solid after cooling at 5°. An analysis sample was recrystallized from ethyl acetate. Melting point: 95° to 97°.

Elementary analysis:

|  | C(%) | H(%) | N(%) |
|---|---|---|---|
| Calculated $C_{17}H_{23}N_3O_3$ | 64.33 | 7.30 | 13.24 |
| Found | 64.53 | 7.35 | 13.27 |

Example 13

2-Methyl-4-[2'-hydroxy-3'-(N-methylpiperazino)]-propoxy-1-(2H)-phthalazinone

This compound was prepared following essentially the same procedure as set forth in Example 12 using 2.32 g. (0.01 mole) of 2-methyl-4-(2',3'-epoxy)-propoxy-1(2H)-phthalazinone and 1.1 g. (0.011 mole) of N-methylpiperazine. An analysis sample was recrystallized from ethyl acetate. Melting point: 144° to 146°.

Elementary analysis:

|  | C(%) | H(%) | N(%) |
|---|---|---|---|
| Calculated $C_{17}H_{24}N_4O_3$ | 61.42 | 7.27 | 16.85 |
| Found | 61.36 | 7.21 | 16.47 |

As indicated hereinbefore, it has been found in accordance with this invention that the novel compounds of the formula I and salts thereof have interesting pharmacological properties. More particularly, such compounds when subjected to standard pharmacological evaluation exhibit marked hypotensive activity in lowering blood pressure. Compounds acting in this way may be expected to be of use as anti-hypertensive agents.

Accordingly, this invention further provides, in another of its aspects, a pharmaceutical composition comprising as an essential active ingredient at least one active compound of the general formula I or a salt thereof in association with a pharmaceutically acceptable carrier therefor.

The compositions of the present invention are preferably administered either orally or rectally. Advantageously, the composition is in a dosage unit form appropriate to the desired mode of administration. For example, the dosage unit may be a tablet, capsule, pill, powder, packet, granule, wafer, elixir, suppository, or a measured quantity of a suspension, solution, a syrup or segregated multiples of the foregoing. The term "dosage unit form" as used herein refers to physically discrete units suitable as unitary dosages for human subjects and animals, each unit containing a predetermined quantity of active material calculated to produce the desired therapeutic effect in admixture, or otherwise in association, with a pharmaceutical carrier therefor, the quantity of the active ingredient being such that one or more units are normally required for a single therapeutic administration or that, in the case of severable units such as scored tablets, at least one fraction such as a half or a quarter of a severable unit is required for a single therapeutic administration.

Advantageously, the compositions of this invention contain the active ingredient in an amount of at least 0.5% and not more than 95% by weight based on the total weight of the composition. Conveniently, the compositions of the invention when in dosage unit form contain 0.5 mg. to 1000 mg., and more conveniently from 5 mg. to 250 mg., of the active ingredient of formula I.

The compositions of the present invention will normally consist of at least one compound of formula I, typically in the form of an acid addition, say, hydrochloride or maleate salt thereof admixed with a carrier or diluted by a carrier, or enclosed or encapsulated by a carrier in the form of a capsule, sachet, catchet, paper or other container. A carrier which serves as a vehicle, excipient or diluent medium for the therapeutically active ingredient may be a solid, semi-solid or a sterile liquid.

Some examples of the carriers which may be employed in the pharmaceutical compositions of the invention are lactose, dextrose, sorbitol, mannitol, starches such as wheat, corn, or potato starch, gum acacia, calcium phosphate, liquid paraffin, cocoa butter, oil of theobroma, alginates, tragacanth, gelatin, syrup B.P., methyl cellulose, polyoxethlene sorbitan monolaurate, methyl and propyl hydroxybenzoates, sterile pyrogen-free water and substantially isotonic saline solution. The choice of carrier is determined by the preferred form of administration, the solubility of the compound and standard pharmaceutical practice. In the case of tablets a lubricant may be incorporated to prevent sticking and binding of the powdered ingredients in the dies and on the punch of the tabletting machine. For such purpose, there may be employed, for example, talc, aluminum, magnesium or calcium stearates polyethylene glycols (Carbowaxes) of suitable molecular weight.

The pharmaceutical compositions of this invention may contain, in addition to the active ingredient of the general formula I, one or more other pharmacologically active ingredients which elicit desirable complementary effects.

Two examples of suitable pharmaceutical compositions according to this invention are presented below for the purpose of facilitating a better understanding of this aspect of the invention.

Example A

For oral administration, sugar coated tablets of the following composition were prepared following standard pharmaceutical practice.

| Formulation: Ingredient | Content (gms.) |
|---|---|
| 2-Methyl-4-(2'-hydroxy-3-piperidino)-propoxy-1 (2H)-phthalazinone | 25 |
| Lactose | 60 |
| Starch | 50 |
| Sugar | 75 |
| Talc | 5 |
| Magnesium stearate | 5 |

Example B

Hard gelatin capsules were made following standard pharmaceutical practice from a mixture of the following ingredients:

| Formulation: Ingredient | Gms. |
|---|---|
| 2-Methyl-4-[2'-hydroxy-3'-(3-dimethylaminopropylamino)]-propoxy-1 (2H)-phthalazinone | 100 |
| Calcium phosphate | 20 |

In the foregoing Examples A and B, the active ingredient specified may be wholly or partly replaced by another pharmacologically active compound of the invention.

The novel method of the invention for alleviating hypertensive conditions in warm-blooded animals comprises administering to the animals an effective amount of at least one compound of the formula I and their non-toxic pharmaceutically acceptable acid addition salts. The usual effective dose of said compounds is between about 0.01 to 5 mg./kg. of body weight of the warm-blooded animals.

While in the foregoing specification various embodiments of this invention have been set forth and specific details elaborated upon for the purpose of illustration, it will be apparent to those skilled in the art that this invention is susceptible to other embodiments and that many of the details may be varied widely without departing from the spirit and scope of the invention as defined in the appended claims.

What we claim is:

1. A phthalazine derivative of the formula:

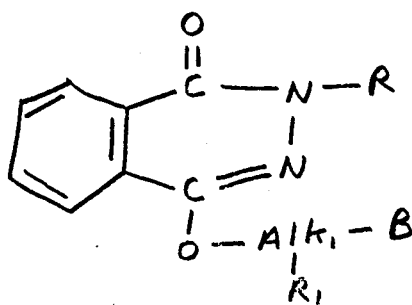

or an acid addition salt thereof or a quaternary ammonium salt thereof; wherein R is lower alkyl, aryl or lower aralkyl; wherein $R_1$ is a free hydroxyl group; and wherein B is an amino group selected the class consisting of

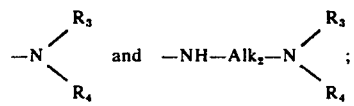

wherein $Alk_1$ represents a straight or branched-chain lower alkylene group interposing at least 3 carbon atoms in a direct or straight line between the oxygen and nitrogen atoms; wherein $Alk_2$ is a lower alkylene group; and wherein $R_3$ and $R_4$, when taken separately, are the same or different, and each is hydrogen, lower alkyl, aryl or lower aralkyl or, when taken together with the nitrogen atom to which they are attached, is a 5 or 6-membered heterocyclic ring, said heterocyclic ring formed by $R_3$ and $R_4$ can be interrupted by an oxygen atom or a nitrogen atom.

2. A phthalazine derivative as claimed in claim 1 wherein $R_3$ is hydrogen, lower alkyl, aryl or lower aralkyl, and wherein $R_4$ is hydrogen, lower alkyl, aryl or lower aralkyl.

3. A phthalazine derivative as claimed in claim 1 wherein $R_3$ and $R_4$, when taken together with the nitrogen atom to which they are attached, is a 5 or 6-membered heterocyclic ring.

4. A phthalazine derivative as claimed in claim 3 wherein R is a lower alkyl group; wherein $Alk_1$ is a 2-hydroxy-propylene group; wherein $R_3$ and $R_4$, when taken together with the nitrogen atom to which they are attached, are pyrrolidino, piperidino, morpholino, piperazino or 4-(lower alkyl)-piperazino.

5. A phthalazine derivative as claimed in claim 1 wherein at least one of $R_3$ or $R_4$ is hydrogen or lower alkyl, wherein $R_3$ or $R_4$, within the limitations of the preceding proviso, can be aryl or lower aralkyl.

6. A phthalazine derivative as claimed in claim 5 wherein $R_3$ and $R_4$ are the same or different and are hydrogen or lower alkyl.

7. A phthalazine derivative as claimed in claim 6 wherein B is

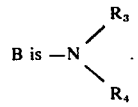

8. A phthalazine derivative as claimed in claim 7 wherein $R_3$ and $R_4$ are hydrogen.

9. A phthalazine derivative as claimed in claim 7 wherein $R_3$ and $R_4$ are lower alkyl.

10. A phthalazine derivative as claimed in claim 6 wherein B is

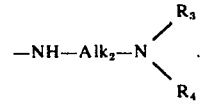

11. A phthalazine derivative as claimed in claim 10 wherein $R_3$ and $R_4$ are hydrogen.

12. A phthalazine derivative as claimed in claim 10 wherein $R_3$ and $R_4$ are lower alkyl.

13. 2-Methyl-4-(2'-hydroxy-3'-isopropylamino)-propoxy-1(2H)-phthalazinone as claimed in claim 1.

14. 2-Methyl-4-[2'-hydroxy-3'-(tert.-butylamino)]-propyl-1-(2H)-phthalazinone as claimed in claim 1.

15. 2-Methyl-4-[2'-hydroxy-3'-(3-phenyl-1-propylamino)]-propoxy-1 (2H)-phthalazinone as claimed in claim 1.

16. 2-Methyl-4-[2'-hydroxy-3'-(sec.-butylamino)]-propoxy-1-(2H)-phthalazinone as claimed in claim 1.

17. 2-Methyl-4-[2'-hydroxy-3'-dimethylamino)]-propoxy-1(2H)-phthalazinone as claimed in claim 1.

18. 2-Methyl-4-(2'-hydroxy-3'piperidino)-propoxy-1(2H)-phthalazinone as claimed in claim 1.

19. 2-Methyl-4-[2'-hydroxy-3'-(N-methyl piperazino)]-propoxy-1(2H)-phthalazinone as claimed in claim 1.

20. 2-Methyl-4-[2'-hydroxy-3'-(3-dimethylaminopropylamino)]-propoxy-1(2H)-phthalazinone as claimed in claim 1.

21. 2-Methyl-4-[2'-hydroxy-3'-(3-diethylaminopropylamino)]-propoxy-1(2H)-phthalazinone as claimed in claim 1.

22. 2-Methyl-4-[2'-hydroxy-3'-(unsym.-dimethylethylenediamine)]-propoxy-1(2H)-phthalazinone as claimed in claim 1.

23. 2-Methyl-4-[2'-hydroxy-3'-(N,N-diethylethylenediamine)]-propoxy-1(2H)-phthalazinone as claimed in claim 1.

24. 2-Methyl-4-[2'-hydroxy-3'-(N-2-aminoethyl)-morpholino]-propoxy-1(2H)-phthalazinone as claimed in claim 1.

25. 2-Methyl-4-[2'-hydroxy-3'-(N-3-amino-propyl)-morpholino)]-propoxy-1(2H)-phthalazinone as claimed in claim 1.

* * * * *